(12) United States Patent
Tamaki (10) Patent No.: US 11,197,984 B2
(45) Date of Patent: Dec. 14, 2021

(54) MICRONEEDLE ARRAY AND MANUFACTURING METHOD OF SAME

(71) Applicant: FUJIFILM Corporation, Tokyo (JP)

(72) Inventor: Kenichiro Tamaki, Kanagawa (TW)

(73) Assignee: FUJIFILM Corporation, Tokyo (JP)

( * ) Notice: Subject to any disclaimer, the term of this patent is extended or adjusted under 35 U.S.C. 154(b) by 71 days.

(21) Appl. No.: 16/777,902

(22) Filed: Jan. 31, 2020

(65) Prior Publication Data

US 2020/0246602 A1    Aug. 6, 2020

(30) Foreign Application Priority Data

Jan. 31, 2019 (JP) .............................. JP2019-015976

(51) Int. Cl.
  *A61M 37/00* (2006.01)

(52) U.S. Cl.
  CPC ... *A61M 37/0015* (2013.01); *A61M 2037/003* (2013.01); *A61M 2037/0023* (2013.01); *A61M 2037/0053* (2013.01)

(58) Field of Classification Search
  CPC ...... A61M 37/0015; A61M 2037/0023; A61M 2037/003; A61M 2037/0053; A61M 2205/6063
  See application file for complete search history.

(56) References Cited

U.S. PATENT DOCUMENTS

| | | | |
|---|---|---|---|
| 10,456,569 | B2 | 10/2019 | Wakamatsu |
| 2012/0276344 | A1 | 11/2012 | Keddie et al. |
| 2013/0072902 | A1* | 3/2013 | Takada ................... A61K 45/06 604/506 |
| 2017/0361082 | A1 | 12/2017 | Okano et al. |
| 2018/0078513 | A1* | 3/2018 | Ueno ................ A61M 37/0015 |

FOREIGN PATENT DOCUMENTS

| | | |
|---|---|---|
| EP | 3320945 | 5/2018 |
| EP | 3348256 | 7/2018 |
| JP | 2013509479 | 3/2013 |
| JP | 2016166769 | 9/2016 |
| JP | 2016168325 | 9/2016 |
| JP | 2018088995 | 6/2018 |
| WO | 2017006958 | 1/2017 |

OTHER PUBLICATIONS

"Search Report of Europe Counterpart Application", dated Jul. 7, 2020, p. 1-p. 9.
"Office Action of Europe Counterpart Application", dated May 28, 2021, pp. 1-3.
"Office Action of Japan Counterpart Application" with English translation thereof, dated Sep. 27, 2021 p. 1-p. 88.

* cited by examiner

*Primary Examiner* — Amber R Stiles
(74) *Attorney, Agent, or Firm* — JCIPRNET (57) ABSTRACT

Provided are a microneedle array capable of improving the visibility of an appearance inspection, and a manufacturing method of the same.
A microneedle array is a microneedle array including: a sheet portion having a first surface and a second surface which oppose each other; and a plurality of needle portions arranged on the first surface of the sheet portion, in which the second surface of the sheet portion is configured by a rough surface having peak portions and valley portions, and an average transmittance of the sheet portion in a wavelength range of 300 nm to 740 nm is 75% or less.

11 Claims, 8 Drawing Sheets

MICRONEEDLE ARRAY AND MANUFACTURING METHOD OF SAME

CROSS-REFERENCE TO RELATED APPLICATIONS

The present application claims priority under 35 U.S.C. § 119 to Japanese Patent Application No. 2019-015976, filed on Jan. 31, 2019. The above application is hereby expressly incorporated by reference, in its entirety, into the present application.

BACKGROUND OF THE INVENTION

1. Field of the Invention

The present invention relates to a microneedle array and a manufacturing method of the same, and more particularly to a technique regarding an improvement in the visibility of an appearance inspection.

2. Description of the Related Art

As a method of administering a drug into the human body, a method using a microneedle array in which needle portions (also referred to as "microneedles") having a high aspect ratio are formed has been widely studied. A microneedle array administers a drug into the human body by inserting needle portions containing the drug into the skin.

Since the microneedle array is used for medical purposes, it is necessary to inspect the shape of the needle portion, the presence or absence of foreign matter, and the like. For example, JP2016-166769A discloses an inspection method in which transparent or translucent microneedles arranged on a transparent or translucent sheet are imaged with a camera in a direction inclined with respect to the surface on which the microneedles are arranged, and the microneedles are inspected based on the obtained image.

SUMMARY OF THE INVENTION

However, in a case where a transparent or translucent microneedle array has gloss, halation is likely to occur during imaging in an appearance inspection of needle shapes and foreign matter in which a light source and a camera is used, and visibility is lowered, so that there is concern that it may become difficult to perform the inspection.

The present invention has been made taking the above circumstances into consideration, and an object thereof is to provide a microneedle array capable of improving the visibility of an appearance inspection of the microneedle array, and a manufacturing method of the same.

A microneedle array according to a first aspect comprises: a sheet portion having a first surface and a second surface which oppose each other; and a plurality of needle portions arranged on the first surface of the sheet portion, wherein the second surface of the sheet portion is configured by a rough surface having peak portions and valley portions, and an average transmittance of the sheet portion in a wavelength range of 300 nm to 740 nm is 75% or less.

According to the first aspect, the visibility of an appearance inspection of the microneedle array can be improved.

In the microneedle array according to a second aspect, the average transmittance is 60% or less. According to the second aspect, in the appearance inspection of the microneedle array, the visibility can be further improved.

In the microneedle array according to a third aspect, the sheet portion contains sodium chondroitin sulfate. According to the third aspect, a material preferable for the sheet portion is defined, and the peak portions and the valley portions can be formed on the second surface of the sheet portion.

In the microneedle array according to a fourth aspect, the needle portion contains a drug. According to the fourth aspect, the drug can be administered into the skin.

A manufacturing method of a microneedle array according to a fifth aspect comprises: a needle portion forming step of, in order to form at least a distal end portion of a needle portion, filling a plurality of recessed portions formed in a mold with a first liquid and drying the first liquid; and a sheet portion forming step of, in order to form a sheet portion having a first surface on which the needle portion is disposed and a second surface opposing the first surface, filling the plurality of recessed portions, in which at least the distal end portion of the needle portion is formed, with a second liquid, and drying the second liquid to form a rough surface having peak portions and valley portions on the second surface and cause an average transmittance of the sheet portion in a wavelength range of 300 nm to 740 nm to be 75% or less.

According to the fifth aspect, the microneedle array capable of improving the visibility of an appearance inspection can be manufactured.

In the manufacturing method of a microneedle array according to a sixth aspect, in the sheet portion forming step, drying is performed at a rate of 50 g/(hr·m$^2$) or less until a concentration of solid contents of the second liquid reaches 80 wt %. According to the sixth aspect, by setting the drying condition of the second liquid within the above-described range, the peak portions and the valley portions can be formed on the second surface of the sheet portion.

In the manufacturing method of a microneedle array according to a seventh aspect, the second liquid contains sodium chondroitin sulfate. According to the seventh aspect, as in the third aspect, a material preferable for the sheet portion is defined, and the peak portions and the valley portions can be formed on the second surface of the sheet portion.

In the manufacturing method of a microneedle array according to an eighth aspect, the first liquid contains a drug. According to the eighth aspect, the drug can be contained in the needle portion.

In the manufacturing method of a microneedle array according to a ninth aspect, the sheet portion forming step includes covering the second liquid with a cap in which an opening is formed. According to the ninth aspect, the drying rate can be reduced.

A manufacturing method of a microneedle array according to a tenth aspect comprises: a needle portion forming step of, in order to form at least a distal end portion of a needle portion, filling a plurality of recessed portions formed in a mold with a first liquid and drying the first liquid; a sheet portion forming step of, in order to form a sheet portion having a first surface on which the needle portion is disposed and a second surface opposing the first surface, filling the plurality of recessed portions, in which at least the distal end portion of the needle portion is formed, with a second liquid, and drying the second liquid; and a processing step of chemically or physically treating the second surface of the sheet portion to form a rough surface having peak portions and valley portions on the second surface and cause an average transmittance of the sheet portion in a wavelength range of 300 mu to 740 mu to be 75% or less.

According to the tenth aspect, as in the fifth aspect, the microneedle array capable of improving the visibility of an appearance inspection can be manufactured.

According to the present invention, the visibility of an appearance inspection of the microneedle array can be improved.

DESCRIPTION OF THE PREFERRED EMBODIMENTS

Hereinafter, preferred embodiments of the present invention will be described with reference to the accompanying drawings. The present invention is described by the following preferred embodiments. Modifications can be made by various methods without departing from the scope of the present invention, and other embodiments than the embodiments can also be used. Therefore, all modifications within the scope of the present invention are included in the appended claims.

Here, in the figures, like elements having similar functions are denoted by like reference numerals. In addition, in this specification, in a case where a numerical value range is expressed using "to", the numerical value range includes the numerical values of the upper limit and the lower limit indicated by "to".

Microneedle Array

An example of a microneedle array (percutaneous absorption sheet) will be described.

Figure 1:
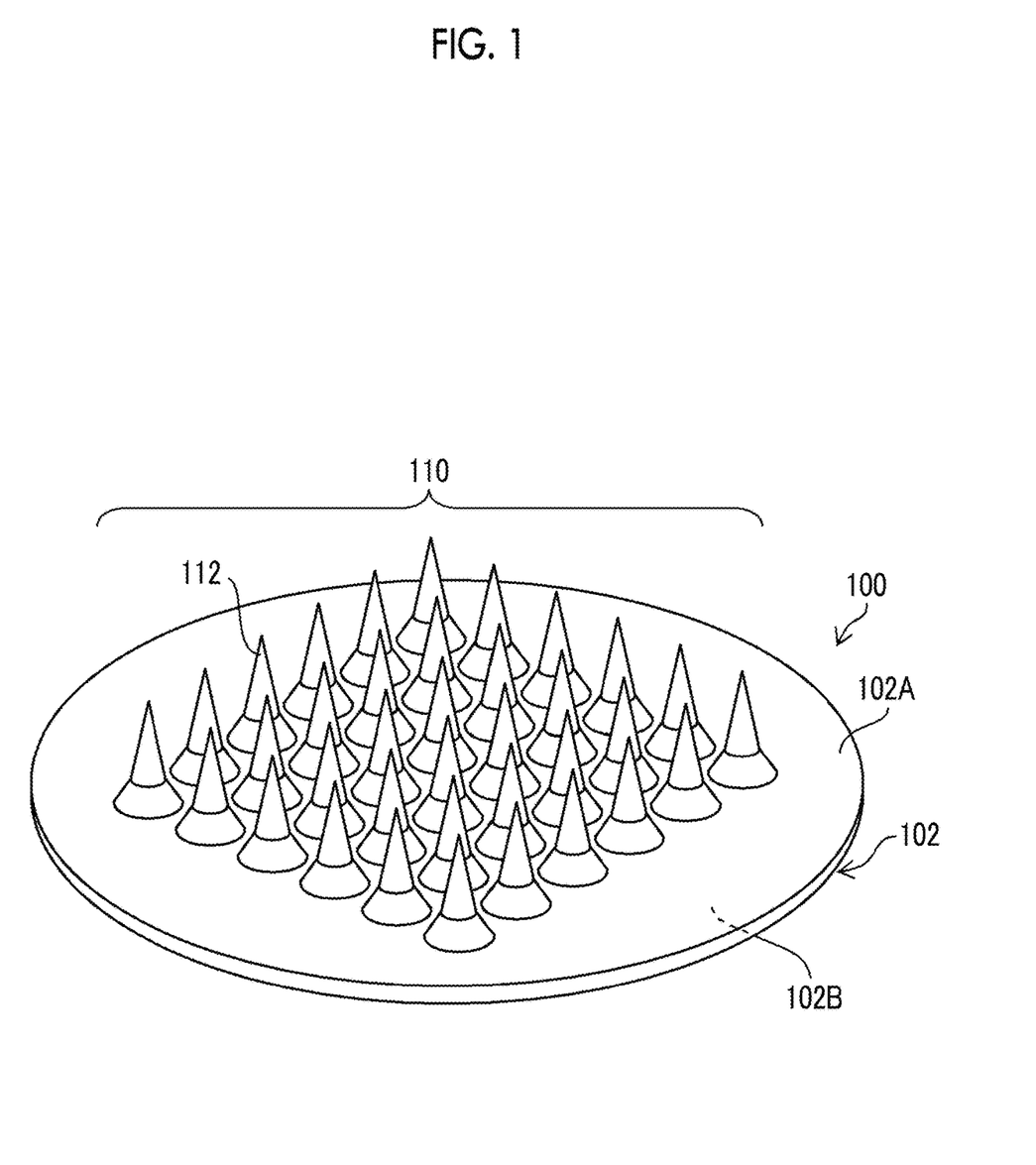
FIG. 1 is a perspective view illustrating a schematic configuration of a microneedle array.

FIG. 1 is a perspective view illustrating an example of a microneedle array 100. The microneedle array 100 of the embodiment corresponds to a patch for one administration. The microneedle array 100 comprises a sheet portion 102 having a first surface 102A and a second surface 102B which oppose each other, and needle portions 112 arranged on the first surface 102A of the sheet portion 102.

The sheet portion 102 has a thin flat shape as a whole with respect to the two opposing first and second surfaces 102A and 102B having a large area. Although the sheet portion 102 illustrated in FIG. 1 is circular in a plan view, the sheet portion 102 may be rectangular, polygonal, elliptical, or the like. Here, the plan view means a state in which the first surface 102A is observed in a direction orthogonal to the first surface 102A.

A plurality of the needle portions 112 are arranged on the first surface 102A of the sheet portion 102 in a predetermined pattern. The plurality of arranged needle portions 112 constitute an array pattern 110. For example, the array pattern 110 can be configured by arranging the plurality of needle portions 112 in a concentric shape, and can also be configured by arranging the plurality of needle portions 112 in a lattice shape. The array pattern 110 is not particularly limited and can be changed as appropriate.

The array pattern 110 is constituted by, for example, 4 to 2500 needle portions 112. However, the number of needle portions 112 is not limited to this number.

The needle portion 112 is configured in a shape having a narrow distal end as compared with the root in contact with the sheet portion 102. Examples of the shape of the needle portion 112 include a cone shape, a polygonal pyramid shape (such as a quadrangular pyramid shape), or a spindle shape. The overall shape of the needle portion 112 may be a cone shape or a polygonal pyramid shape (such as a quadrangular pyramid shape), or may be a structure in which the inclination (angle) of the side surface of the needle portion is continuously changed. Alternatively, a multilayer structure of two or more layers in which the inclination (angle) of the side surface of the needle portion changes discontinuously may also be adopted.

Figure 2:
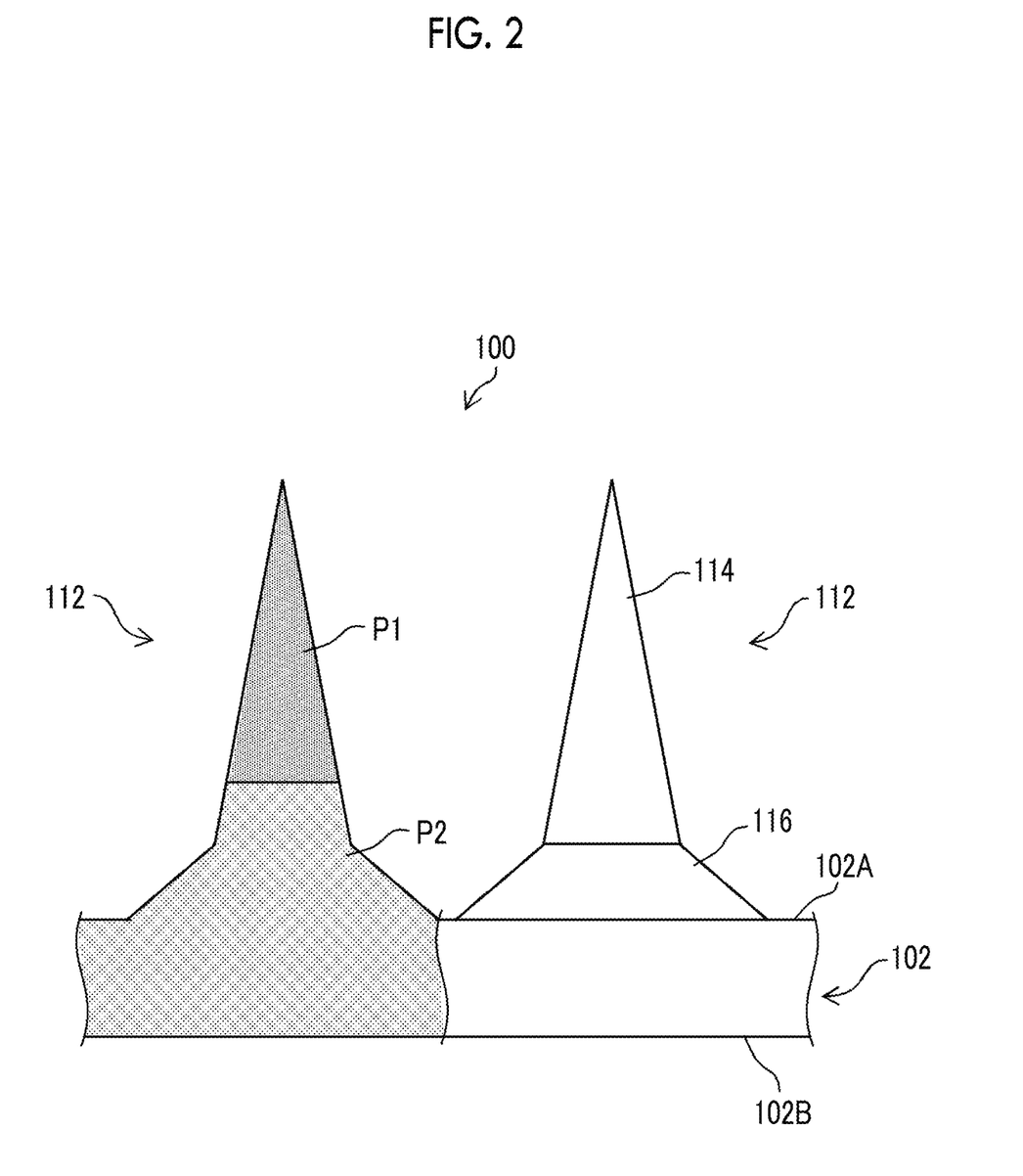
FIG. 2 is an enlarged partial sectional view of the microneedle array.

FIG. 2 is an enlarged partial sectional view of the microneedle array 100. The needle portion 112 includes a needle portion 114 on the distal end side and a frustum portion 116 on the root side. The needle portion 112 has a so-called two-stage structure in which the inclination of the side surface of the needle portion 114 and the inclination of the side surface of the frustum portion 116 discontinuously change in appearance.

The frustum portion 116 has two bottom surfaces and has a three-dimensional structure surrounded by a conical surface. The bottom surface (lower bottom surface) of the two bottom surfaces of the frustum portion 116 having a large area is connected to the sheet portion 102. The bottom surface (upper bottom surface) of the two bottom surfaces of the frustum portion 116 having a small area is connected to the needle portion 114. That is, of the two bottom surfaces of the frustum portion 116, the area of the bottom surface in a direction away from the sheet portion 102 is small.

The needle portion 114 has a bottom surface with a large area and a shape having a narrowest area at the distal end apart from the bottom surface. Since the bottom surface of the needle portion 114 having a large area is connected to the upper bottom surface of the frustum portion 116, the needle portion 114 has a tapered shape in a direction away from the frustum portion 116.

In the form of FIGS. 1 and 2, the needle portion 114 has a cone shape, and the frustum portion 116 has a truncated cone shape. However, the needle portion 114 and the frustum portion 116 are not limited to these shapes. Depending on the degree of insertion of the needle portion 114 into the skin, the shape of the distal end of the needle portion 114 can be appropriately changed to a curved surface, a flat surface, or the like.

The height (length) of the needle portion 112 is represented by the length of a segment from the distal end of the needle portion 112 perpendicular to the sheet portion 102. The height (length) of the needle portion is not particularly limited, but is preferably 50 μm or more and 3000 μm or less, more preferably 100 μm or more and 1500 μm or less, and even more preferably 100 μm or more and 1000 μm or less.

The interval between the needle portions 112 is preferably 0.1 mm or more and 10 mm or less, more preferably 0.2 mm or more and 5 mm or less, and even more preferably 0.3 mm or more and 3 mm or less.

The microneedle array 100 is made of a first polymer P1 containing a drug and a second polymer P2 not containing the drug. The needle portion 114 has a distal end portion made of the first polymer P1 and a root portion made of the second polymer P2. The frustum portion 116 and the sheet portion 102 are made of the second polymer P2.

Containing a drug means containing a drug in an amount that exhibits the drug effect in a case where the body surface is punctured. In addition, not containing a drug means not containing a drug in an amount that exhibits the drug effect. In a case of not containing a drug, the range of the amount of the drug is a range from 0, at which the drug is not contained at all, to the amount at which the drug effect is not exhibited.

The drug is not limited as long as the drug has a function as a drug. In particular, it is preferable to select from pharmaceutical compounds belonging to peptides, proteins, nucleic acids, polysaccharides, vaccines, and water-soluble low-molecular compounds.

The first polymer P1 is not particularly limited, and examples thereof include polysaccharides, polyvinyl pyrrolidone, polyoxyethylene polyoxypropylene glycol, polyethylene glycol, polyvinyl alcohol, and proteins (for example, gelatin). Examples of the polysaccharides include hyaluronic acid, sodium hyaluronate, pullulan, dextran, dextrin, chondroitin sulfate, sodium chondroitin sulfate, cellulose derivatives (for example, water-soluble cellulose derivatives partially modified from cellulose, such as carboxymethyl cellulose, hydroxypropyl cellulose, and hydroxypropyl methylcellulose), hydroxyethyl starch, and gum arabic. The above components may be used singly or as a mixture of two or more.

Among the above components, the first polymer P1 is preferably at least one selected from the group consisting of hydroxyethyl starch, dextran, chondroitin sulfate, sodium chondroitin sulfate, sodium hyaluronate, carboxymethyl cellulose, polyvinyl pyrrolidone, polyoxyethylene polyoxypropylene glycol, polyethylene glycol, and polyvinyl alcohol, and is particularly preferably sodium chondroitin sulfate.

The second polymer P2 is not particularly limited, and examples thereof include polysaccharides, polyvinyl pyrrolidone, polyoxyethylene polyoxypropylene glycol, polyethylene glycol, polyvinyl alcohol, and proteins (for example, gelatin). Examples of the polysaccharides include hyaluronic acid, sodium hyaluronate, pullulan, dextran, dextrin, chondroitin sulfate, sodium chondroitin sulfate, cellulose derivatives (for example, water-soluble cellulose derivatives partially modified from cellulose, such as carboxymethyl cellulose, hydroxypropyl cellulose, and hydroxypropyl methylcellulose), hydroxyethyl starch, and gum arabic. The above components may be used singly or as a mixture of two or more.

Among the above components, the second polymer P2 is preferably at least one selected from the group consisting of hydroxyethyl starch, dextran, chondroitin sulfate, sodium chondroitin sulfate, sodium hyaluronate, carboxymethyl cellulose, polyvinyl pyrrolidone, polyoxyethylene polyoxypropylene glycol, polyethylene glycol, and polyvinyl alcohol, and is particularly preferably sodium chondroitin sulfate.

The first polymer P1 and the second polymer P2 may be the same material or different from each other.

Figure 3:
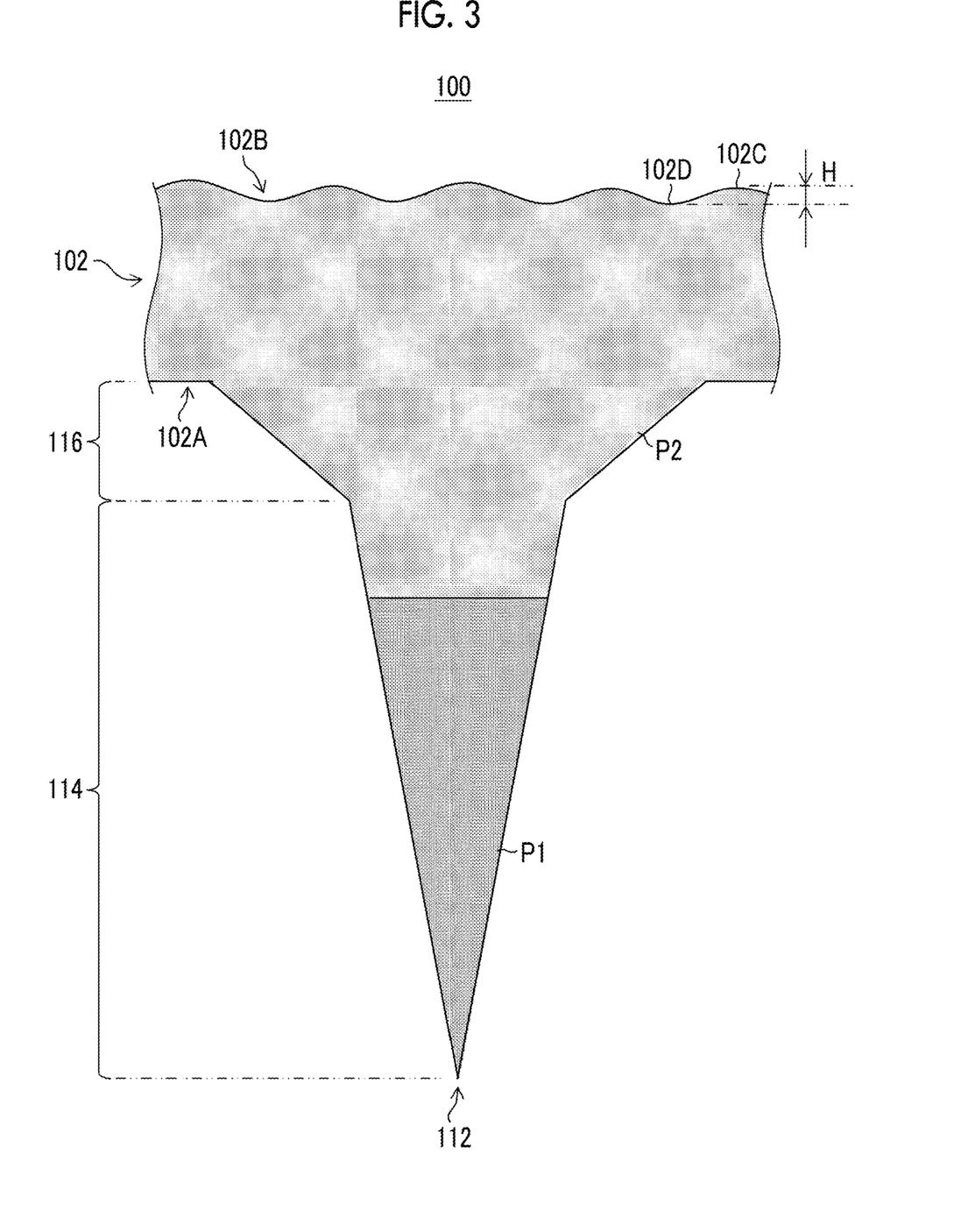
FIG. 3 is an enlarged partial sectional view of a second surface of the microneedle array.

FIG. 3 is an enlarged partial sectional view of the second surface 102B of the microneedle array 100. The second surface 102B of the sheet portion 102 is configured by a rough surface in which a plurality of peak portions 102C and valley portions 102D having different heights H (or depths) and intervals are continuous. It is preferable that the plurality of peak portions 102C and valley portions 102D are provided on the entire second surface 102B. Shape characteristics such as the height H and the intervals between the peak portions 102C and the valley portions 102D can be controlled by a manufacturing method described later.

The microneedle array 100 is manufactured by the first polymer P1 and the second polymer P2 described above. The first polymer P1 and the second polymer P2 are transparent or translucent materials. Therefore, in general, the microneedle array 100 is formed to be transparent or translucent as a whole. However, since the above-described microneedle array 100 has gloss, halation is likely to occur during imaging in an appearance inspection using a light source and a camera.

The microneedle array 100 of the embodiment comprises the sheet portion 102 roughened by the plurality of peak portions 102C and valley portions 102D. The sheet portion 102 of the microneedle array 100 looks cloudy, and as a result, the average transmittance of the sheet portion 102 in a wavelength range of 300 nm to 740 nm is 75% or less. In the microneedle array 100, at least the gloss of the sheet portion 102 can be suppressed. In the appearance inspection of the microneedle array 100, halation during imaging is suppressed. In addition, since halation is suppressed as the average transmittance decreases, the average transmittance is more preferably 60% or less.

The microneedle array 100 of the embodiment can suppress the gloss without using an additive such as a colorant or coloring the needle portion 112. Since the microneedle array 100 is used for medical purposes, it is preferable that addition of a colorant and coloring are not performed.

Here, the average transmittance is an average value of transmittance every 10 nm between 300 nm and 740 nm. The average transmittance of the sheet portion 102 can be measured by the following procedure.

A sample of the microneedle array 100 to be measured is prepared. The sample microneedle array 100 comprises a sheet portion 102 having a diameter of 16 mm and a size of 0.3 mm or more and 0.5 mm or less. An apparatus was prepared by connecting a multi-purpose large-sample compartment (product name "MPC-3100", manufactured by Shimadzu Corporation) to an ultraviolet/visible spectrophotometer (product name "UV-2100" manufactured by Shimadzu Corporation), and this apparatus measures an area where the needle portions 112 of the sheet portion 102 are not formed. With this apparatus, the transmittance of each wavelength light (every 10 nm) between 300 nm and 740 nm is measured. The average transmittance of the sheet portion 102 in a wavelength range of 300 nm to 740 nm can be obtained.

Microneedle Array Inspection Method

Figure 4:
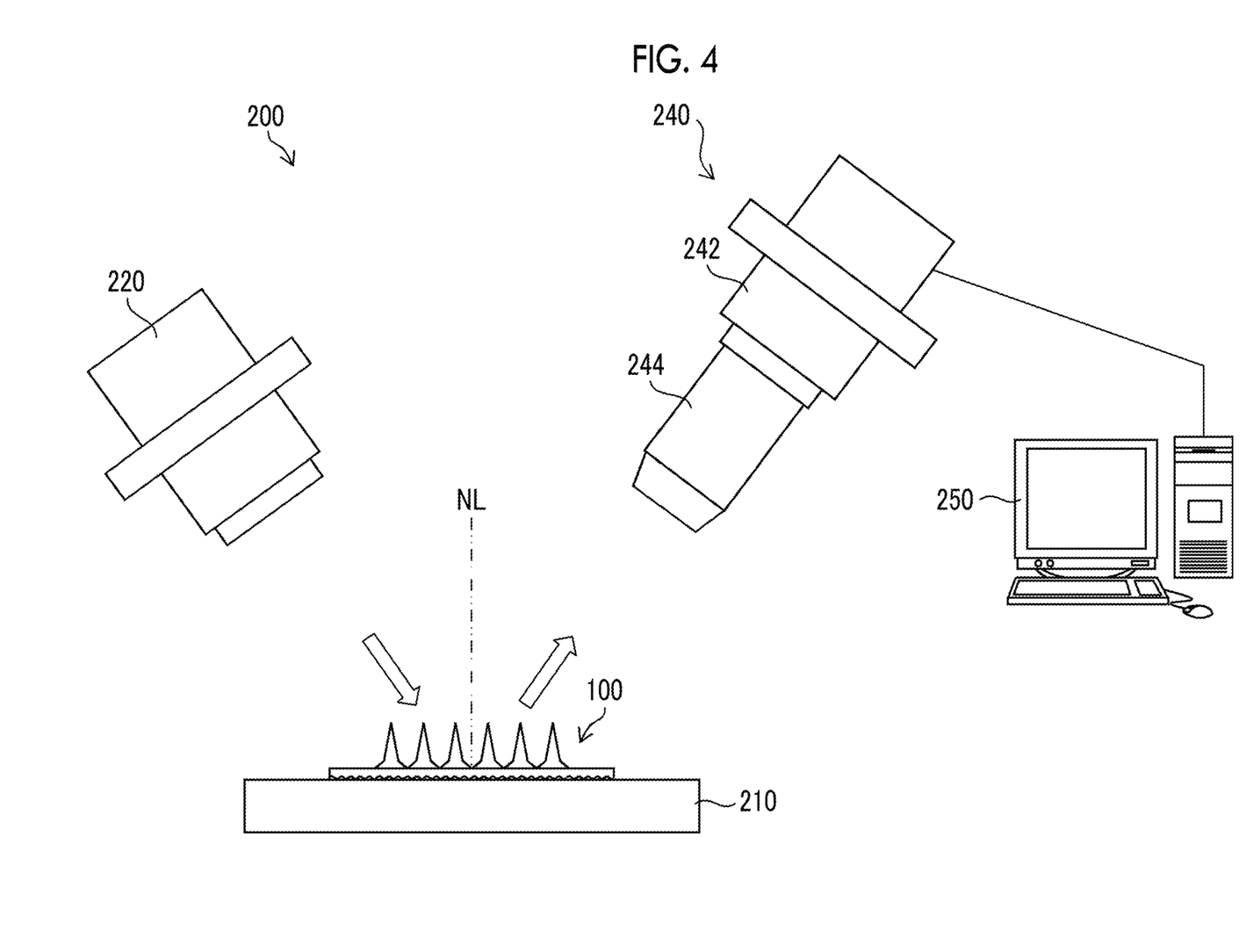
FIG. 4 is a schematic configuration diagram of an inspection apparatus.

A microneedle array inspection method will be described with reference to FIG. 4. As illustrated in FIG. 4, an inspection apparatus 200 comprises a support base 210 that supports the microneedle array 100, an illumination unit 220 that illuminates the microneedle array 100 with illumination light, and an imaging unit 240 that images the microneedle array 100, and an image processing device 250 that inspects the microneedle array 100 based on the image imaged by the imaging unit 240.

The support base 210 supports the microneedle array 100. The support base 210 comprises a flat mounting surface for supporting the microneedle array 100. The microneedle array 100 is placed with the roughened second surface 102B side opposing the mounting surface.

The support base 210 may comprise a drive device (not illustrated). The drive device can move the support base 210 in an X-axis direction, a Y-axis direction, and a Z-axis direction, and can rotate around the Z-axis direction.

The illumination unit 220 comprises a light source and a lens (not illustrated). The light source includes, for example, a white light emitting diode. The illumination unit 220 illuminates the microneedle array 100 with light in a direction inclined at a predetermined angle with respect to the normal line NL of the sheet portion 102 from the needle portion 112 side. The optical axis of the illumination unit 220 is inclined at a predetermined angle with respect to the normal line NL. The illumination unit 220 may comprise a drive mechanism (not illustrated). The drive mechanism can change the angle at which the microneedle array 100 is illuminated.

The imaging unit 240 comprises a camera 242 and a lens 244. The camera 242 is a so-called digital camera, receives light with an imaging element, converts the received light into a digital signal, and outputs the digital signal. The imaging unit 240 images the microneedle array 100 in a direction inclined at a predetermined angle with respect to the normal line NL of the sheet portion 102 from the needle portion 112 side. The optical axis of the imaging unit 240 is inclined at a predetermined angle with respect to the normal line NL. The imaging unit 240 may comprise a drive mechanism (not illustrated). The drive mechanism can change the angle at which the microneedle array 100 is imaged. The illumination unit 220 and the imaging unit 240 are disposed substantially symmetrically about the normal line NL.

The image processing device 250 analyzes the image data of the microneedle array 100 imaged by the imaging unit 240, and inspects the individual needle portions 112 and the sheet portion 102 provided in the microneedle array 100. The image processing device 250 inspects the shape quality of the needle portion 112 and the sheet portion 102, the presence or absence of foreign matter, and the like.

For example, the image processing device 250 is configured by a computer. The computer comprises an arithmetic device and executes a predetermined inspection program. The inspection program causes the computer to function as the image processing device 250. A display, an input device, a recording device, and the like are connected to the computer. The image processing device 250 can execute overall control of the inspection apparatus 200 as well as the inspection program.

The inspection is performed by illuminating the microneedle array 100 placed on the support base 210 with light from the needle portion 112 side, imaging the reflected light by the imaging unit 240 from the needle portion 112 side, and analyzing the obtained image data by the image processing device 250.

Since the second surface 102B of the sheet portion 102 of the microneedle array 100 is roughened, halation during imaging of the microneedle array 100 is suppressed. The visibility of the appearance inspection of the microneedle array 100 can be improved.

Manufacturing Method of Microneedle Array

Figure 5:
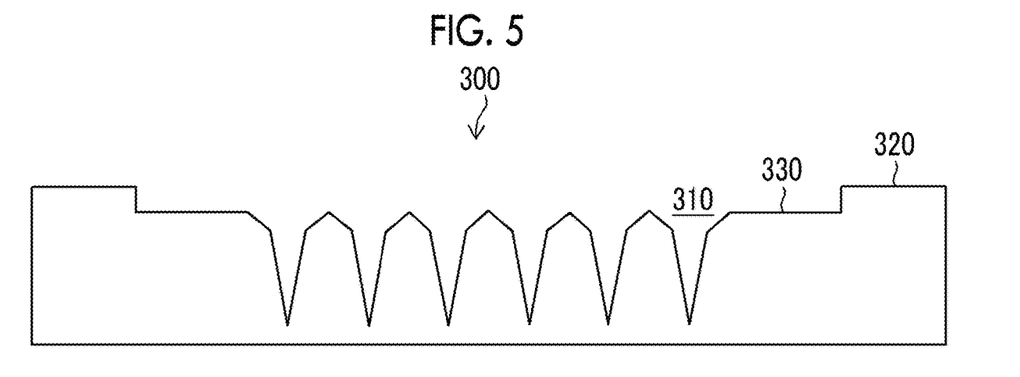
FIG. 5 is a diagram for describing a step of manufacturing the microneedle array.

Next, a manufacturing method of the microneedle array will be described with reference to FIGS. 5 to 10. As shown in FIG. 5, in order to produce the microneedle array 100, a mold 300 in which a plurality of recessed portions 310 are formed is prepared. The recessed portion 310 has an inverted shape of the needle portion 112 of the microneedle array 100. The mold 300 comprises a weir 320 which has a certain height with respect to the opening surface of the recessed portion 310 and surrounds the plurality of recessed portions 310. The mold 300 can be made of, for example, a silicone resin. A flat surface 330 is provided between the recessed portion 310 and the weir 320.

The mold 300 can be produced using a plate precursor (not illustrated) that is a duplicate of the microneedle array 100. The plate precursor is produced by machining a metal substrate using a cutting tool such as a diamond tool. As the metal substrate, stainless steel, an aluminum alloy, Ni, or the like can be used.

The mold 300 in which the plurality of recessed portions 310 are formed is produced by adding a silicone resin before being cured dropwise onto a plate precursor, thereafter curing the silicone resin, and peeling the cured silicone resin from the plate precursor.

Figure 6:
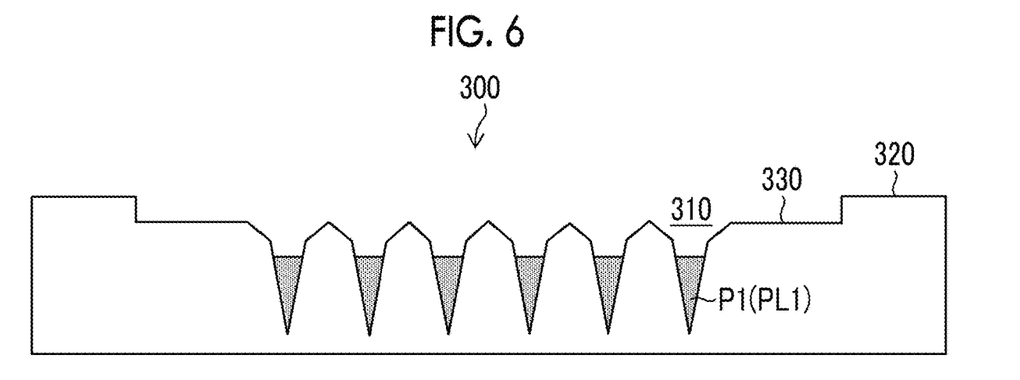
FIG. 6 is a diagram for describing a step of manufacturing the microneedle array.

In the manufacturing of the microneedle array, as illustrated in FIG. 6, the plurality of recessed portions 310 are filled with a first liquid PL1 containing the first polymer P1 and the drug, and then the first liquid PL1 is dried, whereby at least the distal end portion of the needle portion 112 of the microneedle array 100 (not illustrated) is forming of the first polymer P1 containing the drug. In a needle portion forming step, at least the distal end portion of the needle portion 112 made of the first polymer P1 is formed. In the needle portion forming step, the entire needle portion 114 (the root portion and the distal end portion) of the needle portion 112 may be formed, or the entire needle portion 112 (the needle portion 114 and the frustum portion 116) may also be formed. The size of the needle portion 112 formed in the needle portion forming step is determined by the supply amount of the first liquid.

Although not particularly limited, the first liquid PL1 can be caused to fill only the recessed portions 310 by bringing the distal end portion of a slit nozzle into contact with the mold 300. The first liquid PL1 can be caused to fill the recessed portions 310 by supplying the first liquid onto the mold 300 with a nozzle, a dispenser, or the like and then bringing a blade into contact with the mold 300. The first liquid PL1 can be filled by being discharged only to the recessed portions 310 from the nozzle.

Figure 7:
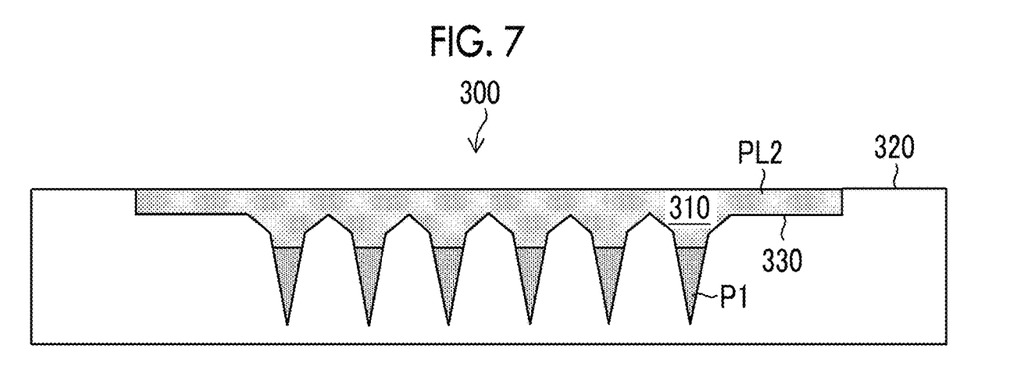
FIG. 7 is a diagram for describing a step of manufacturing the microneedle array.

A sheet portion forming step shown in FIGS. 7 and 8 will be described. As illustrated in FIG. 7, in order to form the sheet portion 102 (not illustrated) having the first surface 102A on which the needle portions 112 are arranged and the second surface 102B opposing the first surface 102A, the plurality of recessed portions 310 in which at least the distal end portion of the needle portion 112 (first polymer P1) is formed is filled with a second liquid PL2 containing the second polymer P2. The second polymer P2 does not contain a drug. The second liquid PL2 is filled beyond the recessed portions 310 and filled until the height thereof is about the same as the weir 320.

Although not particularly limited, the second liquid PL2 is filled by being supplied by a spencer. The second liquid PL2 can be filled by applying spin coating, spray coating, or the like.

Figure 8:
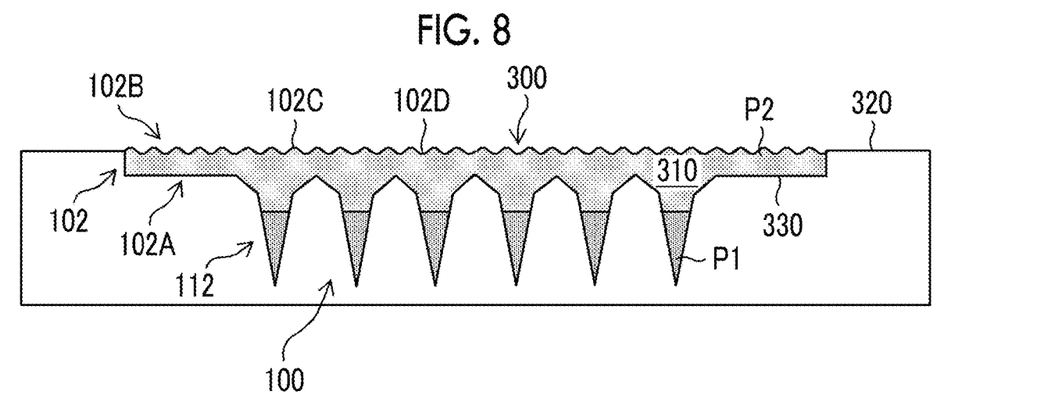
FIG. 8 is a diagram for describing a step of manufacturing the microneedle array.

As illustrated in FIG. 8, the second liquid PL2 filling the mold 300 is dried. In a case where the drying is finished, the second liquid PL2 becomes the second polymer P2, and the microneedle array 100 having the sheet portion 102 and the needle portions 112 in the mold 300 is manufactured. In particular, in a case where the second liquid PL2 contains an aqueous polysaccharide solution, by controlling the drying rate (moisture evaporation rate) and controlling the crystallinity of the polysaccharide, the peak portions 102C and the valley portions 102D are formed on the second surface 102B of the sheet portion 102, whereby the second surface 102B is roughened. The sheet portion 102 appears cloudy.

The drying rate is preferably low, and under the control of the drying rate, a rough surface having the peak portions 102C and the valley portions 102D can be formed on the second surface 102B, and the average transmittance of the sheet portion 102 in a wavelength range of 300 nm to 740 nm can be 75% or less. The drying rate is preferably 50 g/(hr·m$^2$) or less until the concentration of solid contents of the second liquid PL2 reaches 80 wt % in terms of weight percentage. Since the concentration of solid content varies in a thickness direction and an in-plane direction and there is a concentration distribution, the average concentration of solid contents of the entire second liquid PL2 can be used. For example, a change in the concentration of solid contents is preferably calculated by measuring a weight change in the drying step. The drying rate is the mass of water that evaporates per unit time and unit area.

In particular, in a case where the aqueous polysaccharide solution is sodium chondroitin sulfate, the average transmittance of the sheet portion 102 in a wavelength range of 300 run to 740 nm can be 75% or less, and furthermore 60% or less by performing the drying under conditions of a low drying rate.

Figure 9:
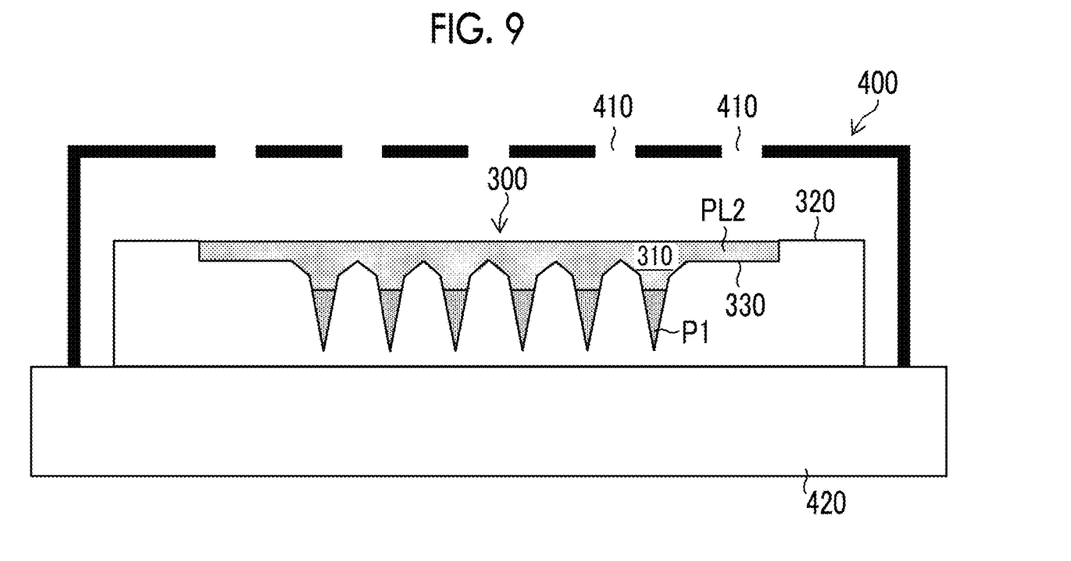
FIG. 9 is a diagram for describing a step of manufacturing the microneedle array.

Next, another sheet portion forming step will be described with reference to FIGS. 9 and 10. For example, as illustrated in FIG. 9, the control of the drying rate of the second liquid PL2 is performed by controlling the temperature and humidity of a drying environment and installing a cap 400 with a plurality of openings 410 formed therein immediately above the mold 300.

The mold 300 and the cap 400 are placed on a support base 420. The cap 400 is disposed at a position covering at least the second liquid PL2 filling the mold 300. The openings 410 are positioned at locations opposing the second liquid PL2. In FIG. 9, the cap 400 covers the entire mold 300. The second liquid PL2 is dried at a low temperature and a high humidity in order to reduce the drying rate. The positions where the openings 410 are provided are not particularly limited.

Figure 10:
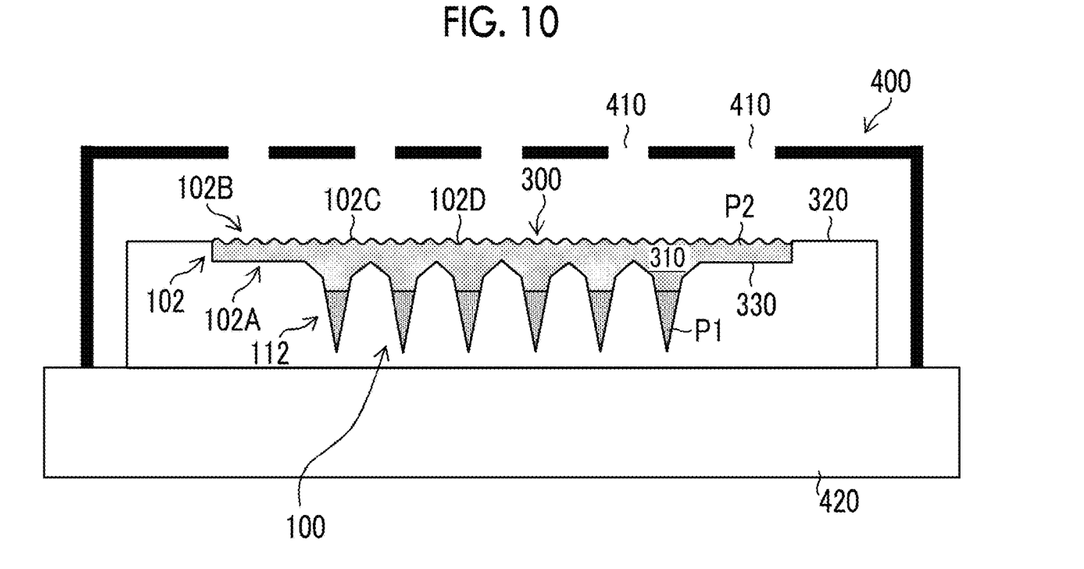
FIG. 10 is a diagram for describing a step of manufacturing the microneedle array.

As illustrated in FIG. 10, in a case where drying is finished, the second liquid PL2 becomes the second polymer P2, and the microneedle array 100 having the sheet portion 102 and the needle portions 112 is manufactured in the mold 300. The peak portions 102C and the valley portions 102D are formed on the second surface 102B of the sheet portion 102, whereby the second surface 102B is roughened. The cap 400 covering the second liquid PL2 suppresses wind hitting the surface of the second liquid PL2, and further increases the relative humidity inside the cap 400. As a result, it is possible to reduce the drying rate.

The control of the drying rate has been described as a method of roughening the second surface 102B of the sheet portion 102 of the microneedle array 100. As a roughening method other than the control of the drying rate, a processing step of performing a chemical treatment such as dry etching or a physical treatment such as sandpaper polishing on the second surface 102B of the sheet portion 102 may be included after the sheet portion forming step.

The control of the drying rate is preferable because damage to the microneedle array 100 is small and no additional step is required compared to a method of chemically or physically roughening the second surface 102B.

EXAMPLES

Hereinafter, the present invention will be described in more detail with reference to examples of the present invention. In addition, the material, use amount, ratio, processing content, processing procedure, and the like described in the following examples can be modified as appropriate without departing from the gist of the present invention. Therefore, the scope of the present invention should not be construed as being limited by the specific examples shown below.

Test 1

A mold having an inverted mold of the shape of the microneedle array is prepared. The mold is made of silicone rubber ("SIL-5930", manufactured by Nusil.) and has a diameter of 20 mm. The mold comprises a surrounding weir with a width of 2 mm and a height of 0.5 mm.

The mold was filled with a second liquid to be a sheet portion. As an aqueous polysaccharide solution to be the second liquid, 250 mg to 300 mg of sodium chondroitin sulfate having a concentration of solid contents of 40 wt % was added dropwise into the mold to fill the mold.

In an environment of 23° C./45% RH (relative humidity), the second liquid was dried at a drying rate of 75 g/(hr·m$^2$) until the concentration of solid contents of the second liquid reached 80 wt %. Thereafter, a microneedle array was produced by peeling the microneedle array from the mold.

Test 2

A microneedle array was produced under the same conditions as in Test 1 except that the drying conditions for the second liquid were changed. In an environment of 24° C./40% RH (relative humidity), the second liquid was dried at a drying rate of 56 g/(hr·m$^2$) until the concentration of solid contents of the second liquid reached 80 wt %.

Test 3

A microneedle array was produced under the same conditions as in Test 1 except that the drying conditions for the second liquid were changed. In an environment of 23° C./45% RH (relative humidity), the second liquid was dried at a drying rate of 50 g/(hr·m$^2$) until the concentration of solid contents of the second liquid reached 80 wt %.

Test 4

A microneedle array was produced under the same conditions as in Test 1 except that the drying conditions for the second liquid were changed. In an environment of 23° C./45% RH (relative humidity), the second liquid was covered with a cap with openings formed therein, and the second liquid was dried at a drying rate of 20 g/(hr·m$^2$) until the concentration of solid contents of the second liquid reached 80 wt %.

Figure 11:
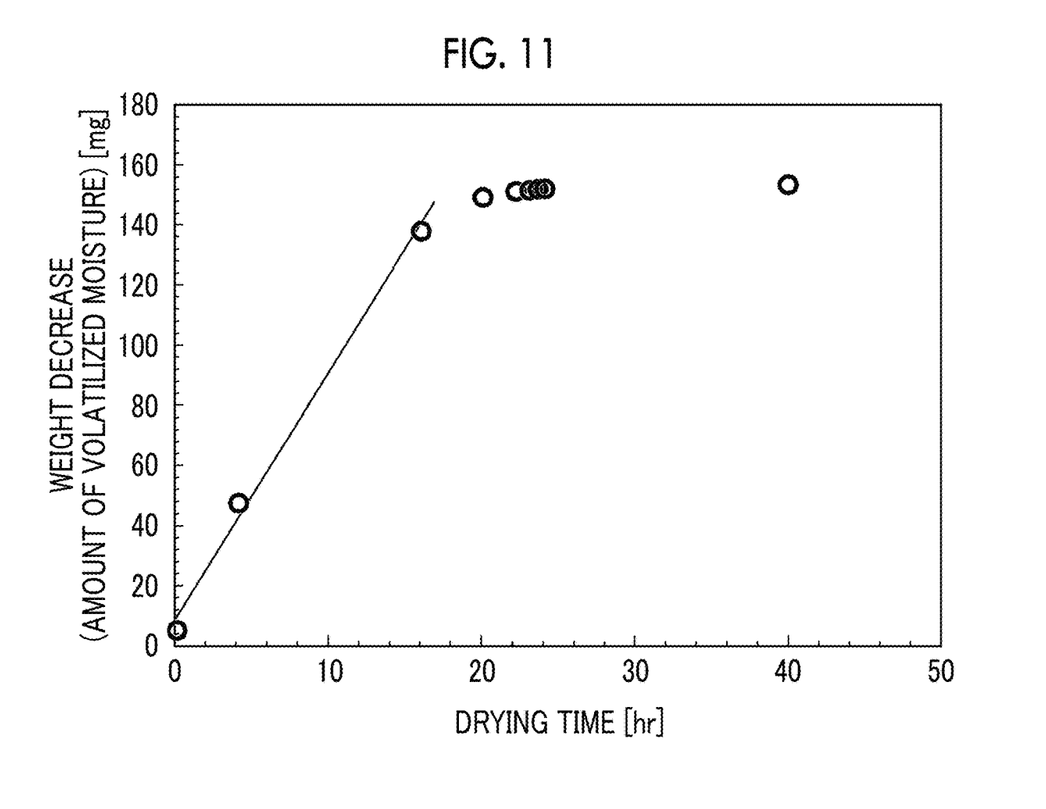
FIG. 11 is a graph for calculating a drying rate.

As shown in FIG. 11, regarding the drying rate of each test, based on a graph with weight decrease (amount of volatilized moisture) (mg) on the vertical axis and drying time (hr) on the horizontal axis, the drying rate was calculated from the gradient of a range in which the weight decrease during the drying step became a linear region. The weight decrease was linear in a range in which the concentration of solid contents of the second liquid was 80 wt % or less.

Evaluation Method

Figure 12:
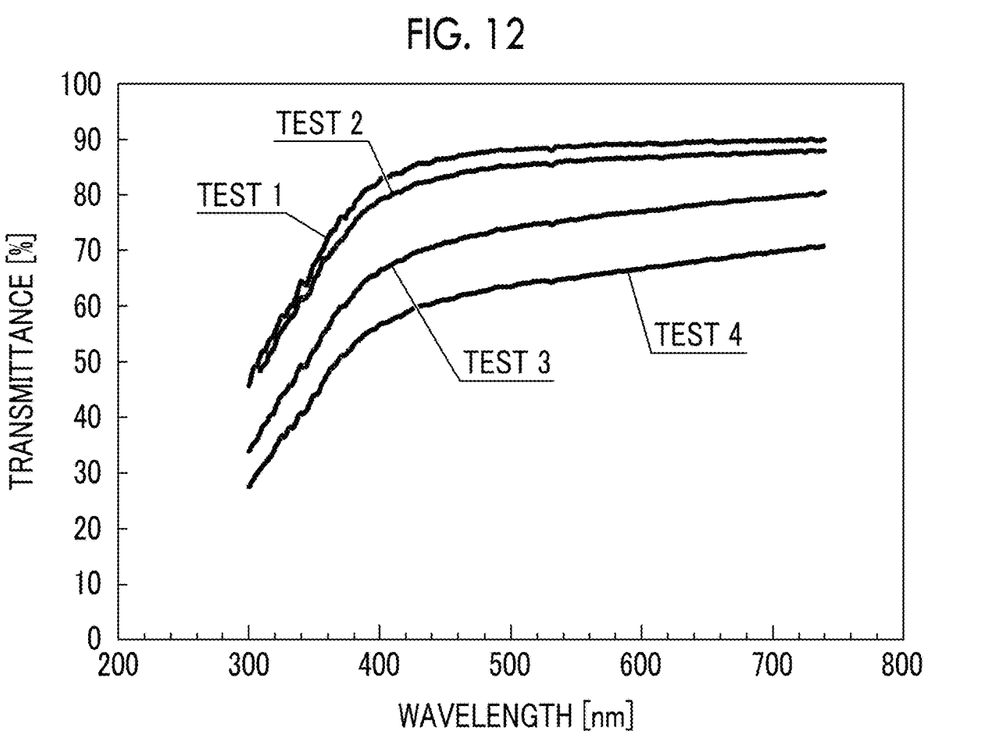
FIG. 12 is a graph plotting transmittance.

With an apparatus prepared by connecting a multi-purpose large-sample compartment (product name "MPC- 3100", manufactured by Shimadzu Corporation) to an ultraviolet/visible spectrophotometer (product name "UV-2100" manufactured by Shimadzu Corporation), the average transmittance of the sheet portion of the microneedle array in a wavelength range of 300 nm to 740 nm was measured. As shown in FIG. 12, the transmittances of Test 1 to Test 4 were plotted on a graph with transmittance (%) on the vertical axis and wavelength (nm) on the horizontal axis.

Evaluation Results

As shown in the graph of FIG. 12, the average transmittance of the sheet portion of the microneedle array of Test 1 was 80.0%. The average transmittance of the sheet portion of the microneedle array in Test 2 was 75.6%. The average transmittance of the sheet portion of the microneedle array in Test 3 was 66.3%. The average transmittance of the sheet portion of the microneedle array in Test 4 was 55.0%. In Test 3 and Test 4, the average transmittance of the sheet portion could be 75% or less.

Figure 13:
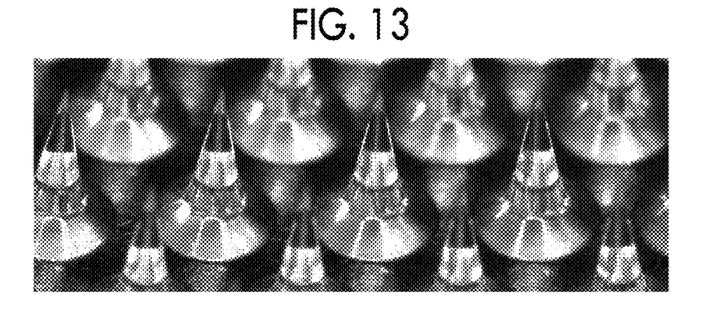
FIG. 13 is an enlarged image of a part of a microneedle array in Test 1.
Figure 14:
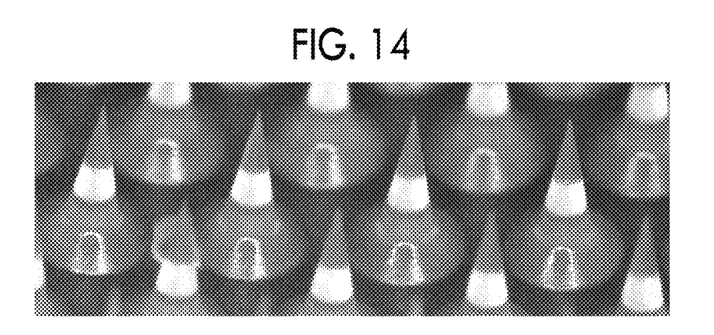
FIG. 14 is an enlarged image of a part of a microneedle array in Test 3.

FIG. 13 is an image of the microneedle array of Test 1, and FIG. 14 is an image of the microneedle array of Test 3. As shown in FIG. 13, in the microneedle array of Test 1, the needle portion and the sheet portion had gloss. On the other hand, as shown in FIG. 14, the needle portion and the sheet portion became cloudy and had almost no gloss. Compared to Test 1, in Test 3, the external shape of the needle portion was clearly confirmed.

Others

The technical scope of the present invention is not limited to the scope described in the above embodiment. The configurations and the like in the embodiments can be appropriately combined between the embodiments without departing from the gist of the present invention.

EXPLANATION OF REFERENCES

100: microneedle array
102: sheet portion
102A: first surface
102B: second surface
102C: peak portion
102D: valley portion
110: array pattern
112: needle portion
114: needle portion
116: frustum portion
200: inspection apparatus
210: support base
220: illumination unit
240: imaging unit
242: camera
244: lens
250: image processing device
300: mold
310: recessed portion
320: weir
330: flat surface
400: cap
410: opening
420: support base
NL: normal line
P1: first polymer
P2: second polymer
PL1: first liquid
PL2: second liquid

What is claimed is:

1. A microneedle array comprising:
a sheet portion having a first surface and a second surface which oppose each other; and
a plurality of needle portions arranged on the first surface of the sheet portion,
wherein the second surface of the sheet portion is configured by a rough surface having peak portions and valley portions,
the sheet portion contains polysaccharide, wherein the crystallinity of the polysaccharide is configured to form the peak portions and valley portions, and
an average transmittance of the sheet portion in a wavelength range of 300 nm to 740 nm is 75% or less.

2. The microneedle array according to claim 1, wherein the average transmittance is 60% or less.

3. The microneedle array according to claim 1, wherein the sheet portion contains sodium chondroitin sulfate.

4. The microneedle array according to claim 1, wherein the needle portion contains a drug.

5. The microneedle array according to claim 1, wherein each of the plurality of needle portions includes a distal end side and a frustum portion, and an inclination of a side surface of the distal end side and an inclination of a side surface of the frustum portion discontinuously change in appearance,
the distal end side has a distal end portion made of a first polymer containing a drug and has a root portion made of a second polymer not containing the drug, and the frustum portion and the sheet portion are made of the second polymer.

6. A manufacturing method of a microneedle array comprising:
a needle portion forming step of, in order to form at least a distal end portion of a needle portion, filling a plurality of recessed portions formed in a mold with a first liquid and drying the first liquid; and
a sheet portion forming step of, in order to form a sheet portion having a first surface on which the needle portion is disposed and a second surface opposing the first surface, filling the plurality of recessed portions, in which at least the distal end portion of the needle portion is formed, with a second liquid, and drying the second liquid to form a rough surface having peak portions and valley portions on the second surface and cause an average transmittance of the sheet portion in a wavelength range of 300 nm to 740 nm to be 75% or less,
wherein, in the sheet portion forming step, drying is performed at a rate of 50 g/(hr·m$^2$) or less until a concentration of solid contents of the second liquid reaches 80 wt % to control the crystallinity of the solid contents.

7. The manufacturing method of a microneedle array according to claim 6,
wherein the second liquid contains sodium chondroitin sulfate.

8. The manufacturing method of a microneedle array according to claim 6,
wherein the first liquid contains a drug.

9. The manufacturing method of a microneedle array according to claim 6,
wherein the sheet portion forming step includes covering the second liquid with a cap in which an opening is formed.

10. A manufacturing method of a microneedle array comprising:

a needle portion forming step of, in order to form at least a distal end portion of a needle portion, filling a plurality of recessed portions formed in a mold with a first liquid and drying the first liquid;

a sheet portion forming step of, in order to form a sheet portion having a first surface on which the needle portion is disposed and a second surface opposing the first surface, filling the plurality of recessed portions, in which at least the distal end portion of the needle portion is formed, with a second liquid containing an aqueous polysaccharide solution, and drying the second liquid; and a processing step of chemically or physically treating the second surface of the sheet portion by controlling a drying rate and controlling a crystallinity of polysaccharide to form a rough surface having peak portions and valley portions on the second surface and cause an average transmittance of the sheet portion in a wavelength range of 300 nm to 740 nm to be 75% or less.

11. The microneedle array according to claim 10, wherein in the sheet portion forming step, drying is performed at a rate of 50 g/(hr·m$^2$) or less until a concentration of solid contents of the second liquid reaches 80 wt %.

\* \* \* \* \*